US005747813A

United States Patent [19]
Norton et al.

[11] Patent Number: 5,747,813
[45] Date of Patent: May 5, 1998

[54] BROADBAND MICROSPECTRO-REFLECTOMETER

[75] Inventors: Adam E. Norton, Palo Alto; Chester L. Mallory, Campbell; Hung V. Pham, San Jose; Paul Rasmussen, Livermore, all of Calif.

[73] Assignee: KLA-Tencop. Corporation, San Jose, Calif.

[21] Appl. No.: 227,482

[22] Filed: Apr. 14, 1994

Related U.S. Application Data

[63] Continuation of Ser. No. 899,666, Jun. 16, 1992, abandoned.

[51] Int. Cl.$^6$ .................................................. G01N 21/33
[52] U.S. Cl. ..................... 250/372; 250/339.11; 356/448
[58] Field of Search ........................... 250/372, 339.11; 356/448, 326, 328

[56] References Cited

U.S. PATENT DOCUMENTS

| Re. 34,783 | 11/1994 | Coates . | |
|---|---|---|---|
| 3,214,596 | 10/1965 | Schwerdt, Jr. et al. . | |
| 3,752,559 | 8/1973 | Fletcher et al. . | |
| 3,975,084 | 8/1976 | Block . | |
| 3,999,855 | 12/1976 | Hirschfeld . | |
| 4,106,856 | 8/1978 | Babish . | |
| 4,158,505 | 6/1979 | Mathisen et al. . | |
| 4,645,349 | 2/1987 | Tabata | 356/382 |
| 4,712,912 | 12/1987 | Messerschmidt . | |
| 4,758,088 | 7/1988 | Doyle . | |
| 4,770,530 | 9/1988 | Van Aken et al. | 356/323 |
| 4,795,256 | 1/1989 | Krause et al. | 356/320 |
| 4,844,617 | 7/1989 | Kelderman et al. | 356/372 |
| 4,848,904 | 7/1989 | Sapp et al. . | |
| 4,899,055 | 2/1990 | Adams . | |
| 4,906,844 | 3/1990 | Hall . | |
| 4,945,220 | 7/1990 | Mallory et al. . | |
| 4,983,823 | 1/1991 | Isobe . | |
| 5,067,805 | 11/1991 | Corle et al. . | |

FOREIGN PATENT DOCUMENTS

| 29 05 727 A1 | 11/1979 | Germany | 356/448 |
|---|---|---|---|
| 57-106846 | 7/1982 | Japan | 356/326 |
| 1-308930 | 12/1989 | Japan | 356/328 |

Primary Examiner—Constantine Hannaher
Attorney, Agent, or Firm—Majestic, Parsons, Siebert & Hsue

[57] ABSTRACT

An improved method and apparatus for measuring the relative reflectance spectra of an observed sample (3) and method and apparatus for autofocussing the sample (3). A broadband visible and ultraviolet beam (42) is split into a sample beam (46) and a reference beam (48). The sample beam (46) is reflected off the surface of the sample (3), and the spectrum of the reflected sample beam (46) is compared to the spectrum of the reference beam (48) to determine the relative reflectance spectrum of the sample (3). A video camera (96) is provided for viewing the sample (3). The autofocus system has a course-focus mode and a fine-focus mode. In the course-focus mode, the sample (3) is focused when the centroid of the sample image is centered on a position sensitive detector (99). In the fine-focus mode, the sample is focused when the intensity of light reaching the detector (99) is minimized.

57 Claims, 7 Drawing Sheets

BROADBAND MICROSPECTROREFLECTOMETER

This is a continuation of application Ser. No. 07/899,666, filed Jun. 16, 1992, now abandoned.

BACKGROUND OF THE INVENTION

The present invention relates to the field of small spot spectral reflectometry. More specifically, in one embodiment, the invention provides an improved method and apparatus for obtaining an accurate relative reflectance spectrum from a sample under a microscope. The samples are typically semiconductor wafers which may contain a number of layers over a silicon substrate.

A relative reflectance spectrum has a variety of uses. The thickness of the various films on the wafer can be determined from a relative reflectance spectrum. Also, the reflectance at a single wavelength can be extracted. This is useful where the reflectance of photoresist coated wafers at the wavelength of lithographic exposure tools must be found to determine proper exposure levels for the wafers, or to optimize the thickness of the resist to minimize the reflectance of the entire film stack. The refractive index of the film can also be determined by analysis of an accurately measured reflectance spectrum.

Because of the tight tolerances in the semiconductor arts, an accurate means for measuring the relative reflectance spectrum of a wafer is needed. Typically, monochromatic light or broadband light is reflected off the wafer, and the reflected light is collected and measured. Several difficulties arise when trying to collect light reflected from the sample. First, the sample must be in focus, otherwise the reflected light disperses. Second, the sample must not tilt with respect to the optics if the optics are sensitive to shifts in the reflected light beam or the optics must be designed to be insensitive to sample tilt, otherwise the reflected light will not be fully captured by the instruments detecting the reflected beam. Lastly, the light source itself may vary in intensity and spectrum, thus distorting the reflectance results.

U.S. Pat. No. 4,645,349 (Tabata, 1987) describes a film thickness measuring device which determines the thickness of a film from a measured reflectance spectrum. A broadband light source (16) illuminates a monochromator (19), which, through a partially reflecting mirror (22), illuminates a film (31). The monochromator filters the broadband light by reflecting it off a diffraction grating (20), and the monochromator output wavelength is selected by rotating the diffraction grating with respect to a directional mirror. A reflected beam from the film is reflected back along the original optical path, and is reflected out of the original optical path by the partially reflecting mirror. The reflected beam then illuminates a photo-multiplier tube (26), and the output of the photo-multiplier tube is connected to a graphics device (30), which is also connected to a wavelength output of the monochromator, allowing the graphics device to display a graph of reflectance versus wavelength. However, since a scanning monochromator is used, obtaining the reflectance spectrum is time consuming, and no means is provided to ensure that the intensity of the incident light is uniform over the time period of measurement. Furthermore, the system of Tabata assumes the sample is in focus. If the sample is not in focus, the reflected light may not be sufficiently focused by the objective to provide a useful spectrum. The optics also present special problems, because the diffraction grating must be precisely aligned with the directional mirror. The partially reflecting mirror is also difficult to manufacture with good efficiency when a very wide range of wavelengths are to be used. Even in the best case, the losses due to the partially reflecting mirror are squared, as the light must pass through the element twice.

U.S. Pat. No. 4,844,617 (Kelderman et al., 1989) describes a confocal focus microscope with an autofocus feature. In that confocal microscope, a system of light sources, stops, and light intensity detectors is used to automatically detect the focus of the confocal microscope and adjust the focus to bring a workpiece into focus. Once the workpiece is in focus, light reflected from the surface of the workpiece is directed to a spectrometer. However, in that device, separate sources are required for field illumination, and the direction of focus is not determinable. In addition, a separate source for ultraviolet (UV) light is required, and only a narrow band of UV light is detected.

SUMMARY OF THE INVENTION

In light of these problems, a new apparatus and method for measuring the relative reflectance spectra of samples has been invented. The present invention provides measurement illumination which is split into a sample beam and a reference beam. The sample beam is reflected from the surface of a sample and is directed onto a diffraction grating and a linear photodiode array, or other spectrum detecting means. The first order diffraction beam from the grating is sensed by the linear photodiode array. The reference beam is also focused onto the diffraction grating and a second linear photodiode array senses the reference spectrum. By dividing the reference spectrum at each wavelength by the spectrum from the sample, the relative reflectance spectrum of the sample is found. The reference spectrum is used to eliminate the effects of a shift in the spectrum or a variation intensity of the illumination. The relative reflectance spectrum can be used to compare the reflectance of one sample relative to another sample at any measured wavelength. The absolute reflectance can be determined by comparing the relative reflectance spectrum to a known reflectance standard such as bare silicon.

The measurement illumination is split into the sample beam and the reference beam by a totally reflecting mirror placed across one half of the optical path of the measurement illumination. An autofocus mechanism is provided, with a coarse focus mode and a fine focus mode. In the coarse focus mode, the autofocus mechanism uses the semicircular or semi-annular sample beam to quickly focus the sample under a microscope objective. The sample beam falls on the center of a position sensitive detector if the sample is in focus, otherwise it falls to one side. The side it falls on indicates whether the out-of-focus condition is due to the sample being too close to or too far from the microscope objective.

In the fine focus mode, apertures of similar size at each of two focal points of the microscope objective are used. A focussing beam, which is from the same light source as the measurement illumination, passes through one aperture, passes through the objective, is reflected off the sample, and is focused again onto the second aperture. If the sample is in focus, the light from the first aperture will pass through the second aperture. Consequently, the light falling on the stop which forms the second aperture indicates whether the sample is in focus by the amount of light falling on the stop. This light falling on the stop is reflected to an intensity detector. The autofocus mechanism adjusts the focus of the sample so as to minimize the light falling on the detector.

The present invention has many applications, such as measuring reflectance spectra, measuring refractive indices, measuring film thicknesses, and determining lithographic exposure times, to name a few.

A further understanding of the nature and advantages of the inventions herein may be realized by reference to the remaining portions of the specification and the attached drawings.

DESCRIPTION OF THE PREFERRED EMBODIMENTS

Figure 1:
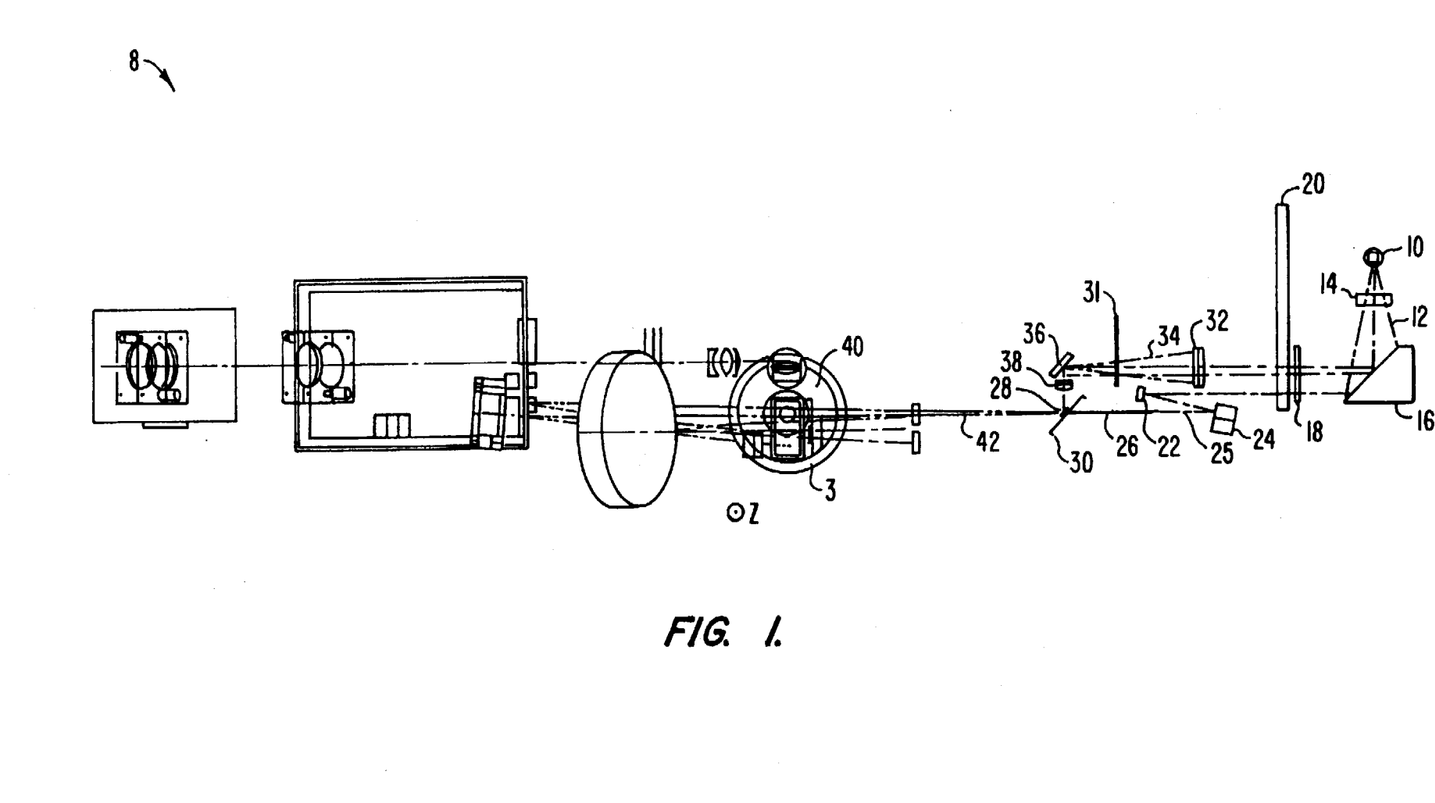
FIG. 1 is a top view of an embodiment of a broadband small spot spectral reflectometer, camera and autofocus apparatus according to the present invention.
Figure 2:
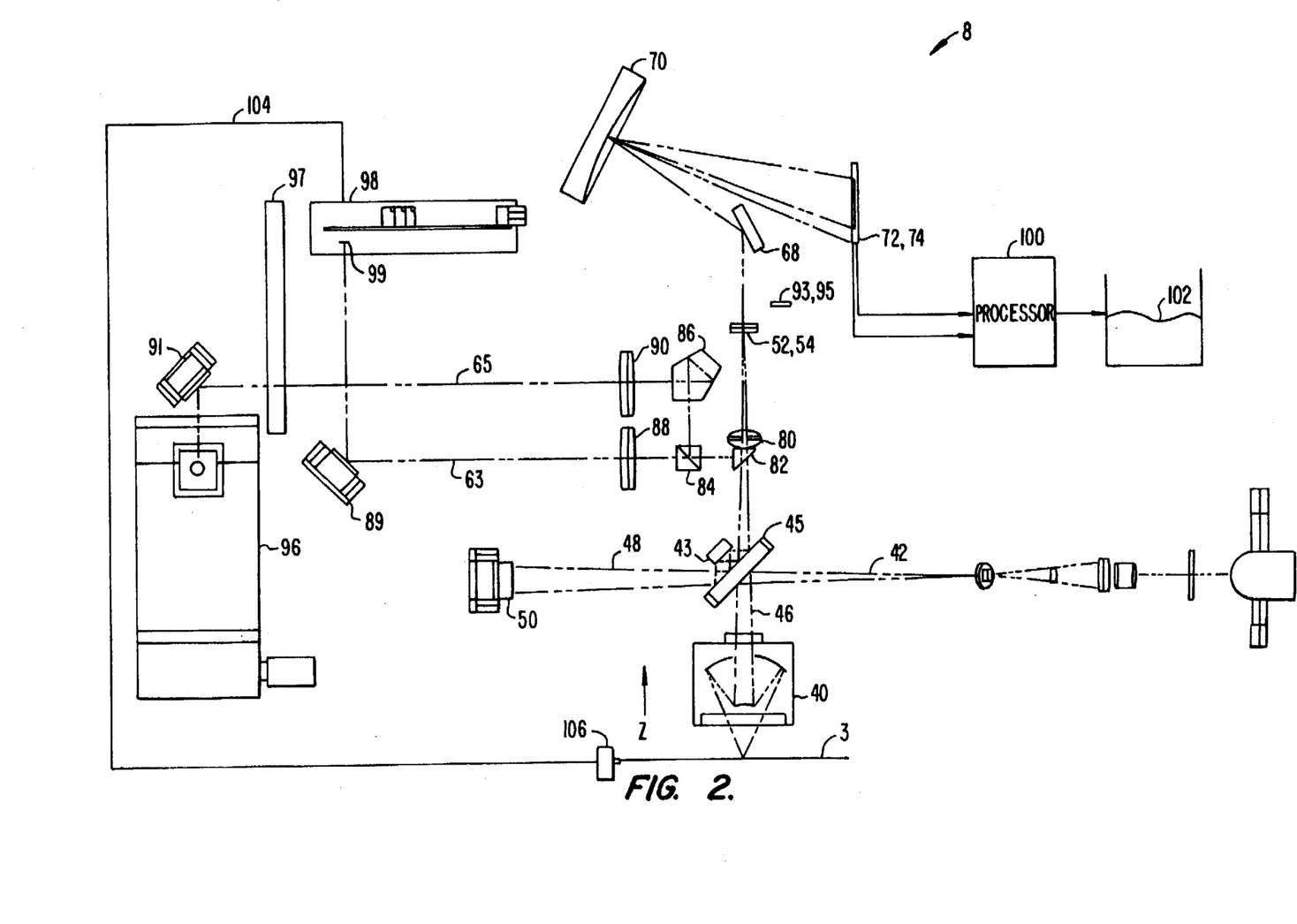
FIG. 2 is a front view of the apparatus of FIG. 1.
Figure 3:
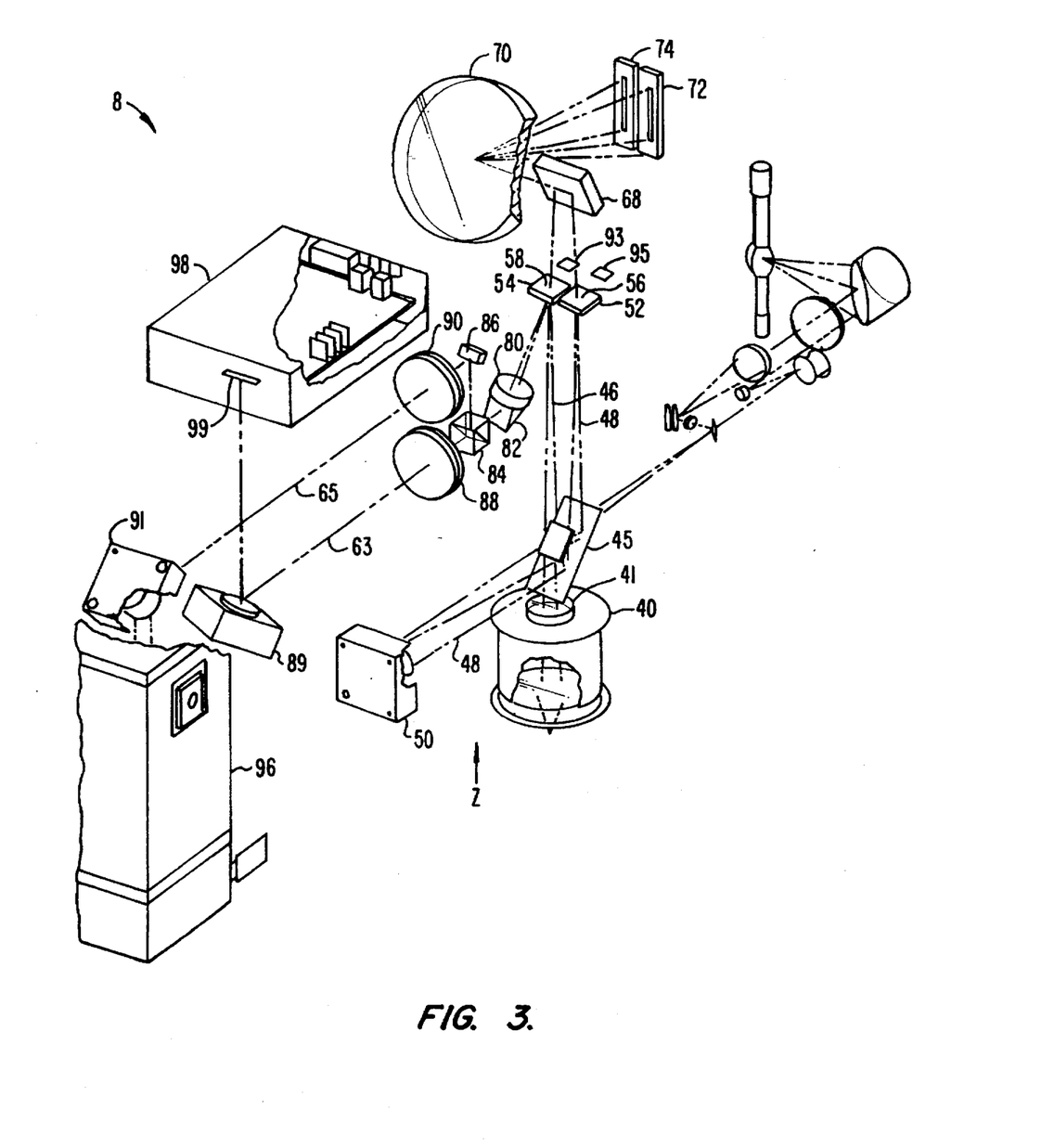
FIG. 3 is an isometric view of the apparatus of FIG. 1.

FIGS. 1, 2 and 3 each show the same embodiment of an optical system according to the present invention, but from different angles. The elements are explained below in conjunction with the figure which most clearly shows their placement with respect to other elements, and for clarity, some elements have been omitted from some figures.

Referring to FIG. 1, an optical system 8 for measuring the relative reflectance spectrum of a wafer 3 and focussing wafer 3 with respect to the optical system includes an illumination subsystem, a reflectometer subsystem, a viewing subsystem, and an autofocus subsystem, wherein any given optical element may be part of more than one subsystem.

The illumination subsystem includes a lamp 10, typically a xenon arc lamp, which emits a light beam 12 of visible and/or UV light, a lamp housing window 14, an off-axis paraboloid mirror 16, a flip-in UV cutoff filter 18, a color filter wheel 20, a flat mirror 22, a concave mirror 24, a large-core silica fiber 26, an aperture mirror 28 with a flip-in 40 µm fine focus aperture 30, a large achromat 32, a field illumination shutter 31, a fold mirror 36, and a small achromat 38.

Figure 9:
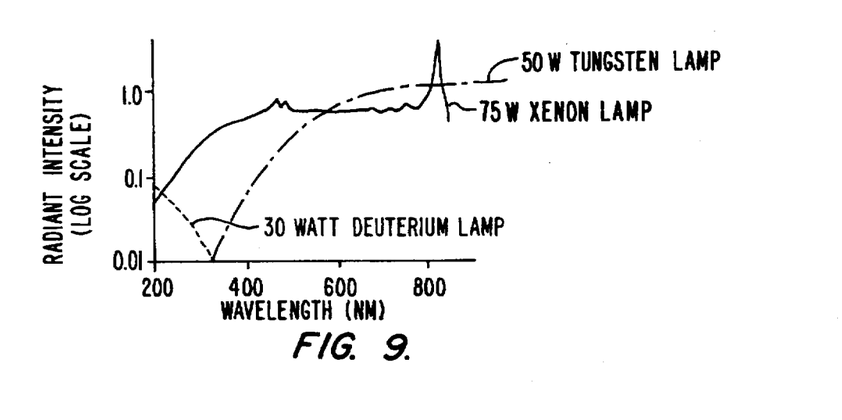
FIG. 9 is a graph of the output of various lamp types.

The illumination system provides a combined beam 42 comprising a measurement beam 25 and a field illumination beam 34. Lamp 10 emits light beam 12 through a lamp housing window 14. The lamp housing window is not necessary for optical reasons, however it is provided to contain lamp 10 should the lamp crack and explode. A xenon lamp is preferred over other lamps such as tungsten or deuterium lamps, because a xenon lamp will give a flatter output covering a spectrum from UV to near infrared as shown in the graph of FIG. 9. Typically, a tungsten lamp and a deuterium lamp are used in combination to cover the same spectrum covered by a xenon lamp, however this combination still leaves a gap in brightness in the mid-UV wavelengths. Brightness of the spectrum is important, because with less intensity, light must be collected for longer periods, thus lower intensities slow the measurement process. Normally, xenon lamps are disfavored due to the instability of their intensity and the fact that the arc may shift positions. However, in the present invention both of these drawbacks have been overcome.

Off-axis paraboloid mirror 16 collimates light beam 12, which can be optionally filtered by flip-in UV cutoff filter 18 and color filter wheel 20. Flip-in UV cutoff filter 18 is used in part to limit the spectrum of light beam 12, so that when light beam 12 is dispersed by a diffraction grating, the first and second order diffraction beams do not overlap. Part of light beam 12 is reflected by flat mirror 22 onto concave mirror 24 to form measurement beam 25. Concave mirror 24 focuses measurement beam 25 onto the end of large-core silica fiber 26, which acts as a radial uniformer. Thus, regardless of the intensity pattern in a cross section of measurement beam 25 at the input of large-core silica fiber 26, the output of large-core silica fiber 26 is radially symmetric. Without this radial uniformer, it is possible that the arc in lamp 10 might shift and cause the intensity of light across a cross section of measurement beam 25 to shift causing apparent fluctuations in the relative reflectance spectrum.

Another part of light beam 12, field illumination beam 34, is focused by large achromat 32 near fold mirror 36, causing fold mirror 36 to reflect an image of lamp 10 toward small achromat 38. Small achromat 38 collects the light in field illumination beam 34 before the light reflects off aperture mirror 28. Aperture mirror 28 is a fused silica plate with a reflective coating on one side, with a 150 µm square etched from the reflective coating to provide an aperture for measurement beam 25. The aperture is placed at one conjugate of an objective 40 (see FIG. 2). The field illumination can be turned off by placing field illumination shutter 31 in the optical path of field illumination beam 34.

The narrow measurement beam 25 and wide field illumination beam 34 are rejoined at aperture mirror 28, with field illumination beam 34 reflecting off the front of aperture mirror 28, measurement beam 25 passing through the aperture. The use of flip-in fine focus aperture 30 is explained in detail below.

FIGS. 2 and 3 show more clearly the reflectometer, viewing and autofocus subsystems of optical system 8, including objective 40, a beamsplitter mirror 45, a sample beam 46, a reference beam 48, a concave mirror 50, a flat mirror 43, a reference plate 52 with a reference spectrometer pinhole 56, a sample plate 54 with a sample spectrometer pinhole 58, a second fold mirror 68, a diffraction grating 70, a sample linear photodiode array 72, a reference linear photodiode array 74, a flip-in reference photodiode 95, a flip-in sample photodiode 93, an achromat 80 with a short focal length, a right angle prism 82, a beamsplitter cube 84, a penta prism 86, achromats 88, 90 with long focal lengths, a third fold mirror 89, a focus detector 98, a neutral density filter wheel 97 (not shown in FIG. 3, for clarity), a fourth fold mirror 91, and a video camera 96.

Several magnifications are possible for objective 40. In one embodiment, a 15X Schwarzchild design all-reflective objective, a 4X Nikon CFN Plan Apochromat, color corrected at three wavelengths, and a 1X UV transmissive objective are mounted on a rotatable turret which allows for one of the three objectives to be placed in the optical path of sample beam 46.

The measurement of the relative reflectance spectra of wafer 3 will now be described. A typical relative reflectance spectrum 102 is shown in FIG. 2. When field illumination shutter 31 is placed in the path of field illumination beam 34, combined beam 42 comprises only measurement beam 25. Combined beam 42 is split by beamsplitter mirror 45, a totally reflecting mirror placed so as to deflect half of combined beam 42 towards objective 40, thus forming sample beam 46, the undeflected half of combined beam 42 forming reference beam 48. Importantly, because sample beam 46 and reference beam 48 are derived from the same source, lamp 10, and because combined beam 42 is radially uniform, reference beam 48 and sample beam 46 have proportionally dependent spectral intensities. Furthermore, since beamsplitter mirror 45 is a totally reflecting mirror in half of an optical path rather than a partially reflecting mirror in the entire optical path, a continuous broadband spectrum is reflected with good brightness.

Reference beam 48 does not initially interact with beamsplitter mirror 45, but instead illuminates concave mirror 50. Concave mirror 50 is slightly off-axis, so reference beam 48 is reflected onto the reverse face of beamsplitter mirror 45, where flat mirror 43 re-reflects reference beam 48 into alignment with reference spectrometer pinhole 56. Flat mirror 43 is provided to realign reference beam 48 with sample beam 46 so that both beams pass through their respective spectrometer pinholes substantially parallel. This allows for simpler alignment of the spectrometer element for both channels, since the reference beam enters the spectrometer parallel to the sample beam.

Since reference beam 48 does not interact with the surface of beamsplitter mirror 45 which reflects beam 46, there is no loss in reference intensity as reference beam 48 passed beamsplitter mirror 45. While reference beam 48 does interact with a mirror on the reverse side of beamsplitter mirror 45, these two mirrors are independent, since no light passed through beamsplitter mirror 45. Indeed, in an alternative embodiment where the two reflecting surfaces of beamsplitter mirror 45 cannot easily be placed together on one optical element, the reflecting surfaces exist on separate mirror elements.

The focal length of concave mirror 50 is such that reference beam 48 is in focus at reference spectrometer pinhole 56. The light passing through reference spectrometer pinhole 56 and reflecting off fold mirror 68 is dispersed by diffraction grating 70. The resulting first order diffraction beam is collected by reference linear photodiode array 74, thereby measuring a relative reference spectrum.

Sample beam 46 is reflected off beamsplitter mirror 45 towards objective 40, where sample beam 46 is focused onto wafer 3, and the reflected sample beam 46 is focused by objective 40 onto sample spectrometer pinhole 58. The reflected sample beam 46 does not interact with beamsplitter mirror 45 on the reflected path, because sample beam 46 passed through the space behind beamsplitter mirror 45, where reference beam 48 also passes. The light passing through sample spectrometer pinhole 58 and reflecting off fold mirror 68 is dispersed by diffraction grating 70. As with the reference beam, the resulting first order diffraction beam of the sample beam is collected by sample linear photodiode array 72, thereby measuring the sample spectrum. Because the two beams cross at diffraction grating 70, the photodiode array apparently aligned with sample beam 46 in FIG. 3 is in fact the photodiode array for reference beam 48, and vice versa.

The relative reflectance spectrum can then be simply obtained by dividing the sample light intensity at each wavelength by the relative reference intensity at each wavelength. Typically, this might involve 512 division computations, where 512-diode linear photodiode arrays are used to record the sample and reference spectra. A typical spectrum ranges from 220 nm to 830 nm.

In one embodiment of the present invention, diffraction grating 70 is a concave holographic grating and the spectrometer pinholes are 15 mm apart. The diffraction grating is holographically corrected to image multiple spectra, since the 15 mm spacing does not allow for both beams to be centered on the grating. One such grating is a multiple spectra imaging grating supplied by Instruments S.A. Also, the grating is designed so that the angle of the detector causes reflections off the detector to fall away from the grating.

Figure 4:
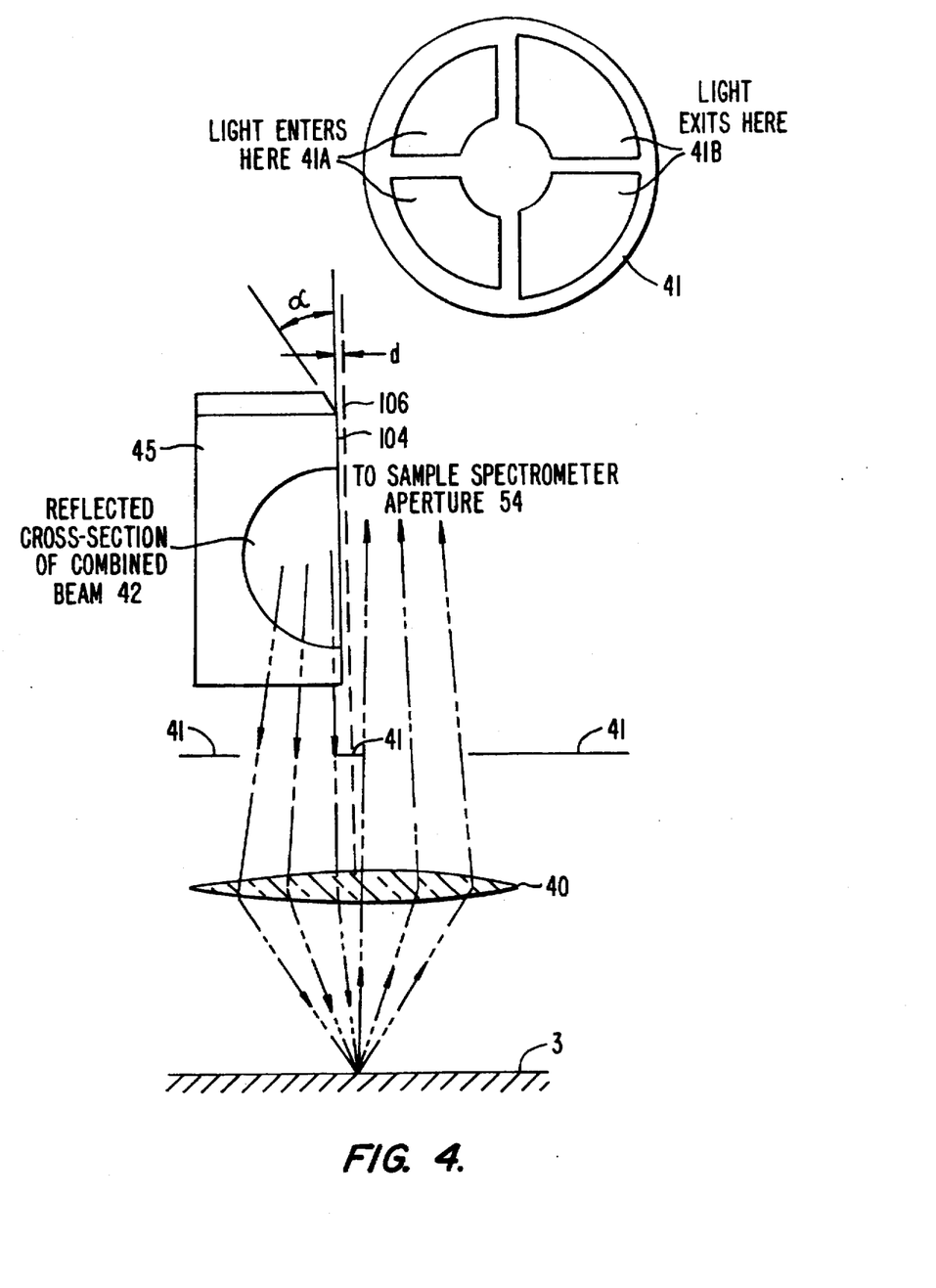
FIG. 4 is a simplified illustration of a beamsplitter mirror and an objective, showing their relative placement.

FIG. 2 shows more clearly the positioning of beamsplitter mirror 45 with respect to objective 40. Combined beam 42, which may include field illumination, is reflected off beamsplitter mirror 45 toward wafer 3. When reflectance spectra measurements and autofocussing are being performed, the field illumination is off to minimize scattered light. An objective pupil stop 41 is placed in the optical path as shown in FIG. 4.

Since light travels both directions through objective 40, objective pupil stop 41 is both an entrance pupil stop and an exit pupil stop. Furthermore, since the light passing through objective 40 has a semicircular cross section, one half (41a) of objective pupil stop 41 is the entrance pupil stop, and the other half (41b) of objective pupil stop 41 is the exit pupil stop. The exit half 41b is slightly larger than the entrance half 41a to allow for deviation of the reflected light due to wafer tilt.

Even with a wide field of view, objective pupil stop 41 does not cause vignetting of the light reflected from wafer 3, since objective pupil stop 41 is in the plane of the back focal point of objective 40. However, since objective pupil stop 41 is in the back focal plane, beamsplitter mirror 45 cannot also be in the back focal plane. To prevent the beamsplitter mirror 45 from vignetting the reflected sample beam 46 when a wide field of view is used, beamsplitter mirror 45 is placed with its edge 104 a slight distance, d, which is about 0.4 to 1.2 mm, from an optical axis 106 of objective 40. Edge 104 is also an acutely angled edge, to avoid interference between the side of beamsplitter mirror 45 and the reflected sample beam 46. The acute angle, α, is about 10° from normal to the mirror surface.

With a concave grating, the local efficiency varies substantially across its face. When wafer 3 tilts, the beam falling on the grating shifts slightly, and changes the signal level. While this effect causes less than a half percent change in reflectance measurements, a map of a wafer's reflectance would be strongly influenced by the flatness of the wafer. To avoid this sensitivity, a different spectrum measuring means is used, namely flip-in photodiodes 93, 95.

While flip-in photodiodes only measure a single intensity value, often the value is a broadband average over a spectrum of interest and provides sufficient information for calculating the full relative reflectance spectrum. Flip-in photodiodes 93, 95 are selected such that they have a broad sensitivity to wavelengths in the UV band, with both photodiodes having substantially similar peak sensitivity wavelengths. The sensitivity of each photodiode drops off gradually for higher and lower wavelengths. Consequently, when the response of sample photodiode 93 is divided by the response of reference photodiode 95, the result is an indication of the reflectance of wafer 3 over wavelengths in the UV band, with the peak sensitivity wavelength having more weight in the measure of reflectance than other wavelengths.

Figure 7:
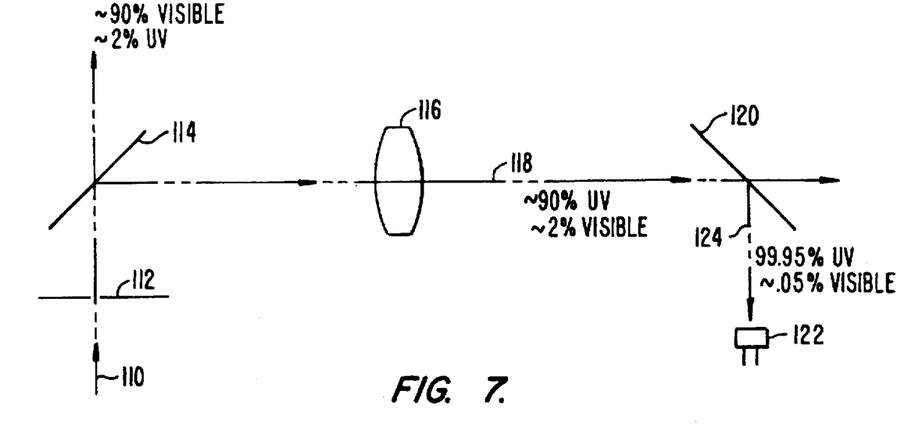
FIG. 7 is a partial illustration of an alternative embodiment of a small spot spectral reflectometer using flip-in dichroic mirrors.

FIG. 7 shows an alternative embodiment of optical system 8, where flip-in photodiodes 93, 95 are fixed outside the reference and sample spectrometer paths, and mirrors are used to optionally deflect the beams onto the fixed photodiodes. FIG. 7 only shows one such system, however two identical systems are used, one for the sample channel and one for the reference channel. Combined visible and UV light in beam 110 passes through entrance pinhole 112, which is equivalent to reference spectrometer pinhole 56 or sample spectrometer pinhole 58. Beam 110 is then partially reflected by flip-in dichroic mirror 114. Most of the visible light passes through flip-in dichroic mirror 112 and most of the UV light is reflected towards a fused silica lens 116. Fused silica lens 116 is provided to increase the optical path for greater flexibility in mounting optical elements, but is not required. Beam 118, containing about 90% of the UV light from beam 110 and only about 2% of the visible light from beam 110, is reflected off stationary dichroic mirror 120, which further filters out visible light. Beam 118 is reflected onto photodiode 122, which measures the intensity of light in beam 124.

In another embodiment, mirror 114 is large enough to reflect both the sample beam and the reflected beam, and mirror 120 is large enough to reflect both the sample beam and the reference beam onto respective photodiodes. Photodiode 122 serves the same purpose as photodiodes 93, 95, however, because of the filtering provided by the dichroic mirrors, the sensitivity of photodiode 122 to visible light is less of a concern. Mirror 114 need not be a flip-in mirror. Mirror 114 can be a fixed mirror, where the attenuation of UV light in the beams directed to diffraction grating 70 is not a problem.

In yet another embodiment, photodiode 122 is fixed to intercept beam 118 without reflection from mirror 120, thus requiring only one dichroic mirror. This arrangement is useful where one mirror sufficiently filters out enough unwanted visible light from beam 110 to avoid intensity detecting errors by photodiode 122.

Because of the innovative arrangement of optical elements used to measure relative reflectance spectra, many of the elements of in the spectra measurement subsystem are also used in the autofocus subsystem. For example, since relative reflectance spectrum measurement in the embodiment shown in the figures uses beamsplitter mirror 45 as opposed to a partially reflecting mirror, the resulting beam reflected from the wafer 3 has a circularly asymmetric cross section. This allows for detecting the direction of focus as well as the relative distance to move objective 40 or wafer 3 to achieve an in-focus condition, whereas with a circularly symmetric cross section, the direction of focus cannot be detected.

The autofocus subsystem of optical system 8 uses the image reflected from sample plate 54. Sample plate 54 is a reflective fused silica plate with an aperture. For simplicity, an identical reflective fused silica plate with an aperture is used as reference plate 52, however reference plate 52 need not be reflecting.

The image reflected from sample plate 54 is also used for viewing wafer 3. As shown in FIGS. 2 and 3, sample beam 46 is partially reflected off sample plate 54, through short focal length achromat 80, right angle prism 82, into beamsplitter cube 84. Beamsplitter cube 84 splits the incoming beam into a camera beam 65 and a focus beam 63. Camera beam 65 is then reflected in penta prism 86, focused by long focal length achromat 90, and reflected into video camera 96 by fold mirror 91. A penta prism is used instead of a mirror, so that the image received by video camera 96 is a non-inverted image of wafer 3.

In the embodiment shown in FIGS. 2 and 3, long focal length achromat 88 and turning mirror 89 direct beam 63 onto detector 99. In an alternative embodiment (not shown), where less space is available, long focal length achromat 88 is replaced by a medium focal length achromat and a negative lens such as a barlow lens. Turning mirrors are used if detector 99 is not mounted in the path of beam 63.

Figure 8:
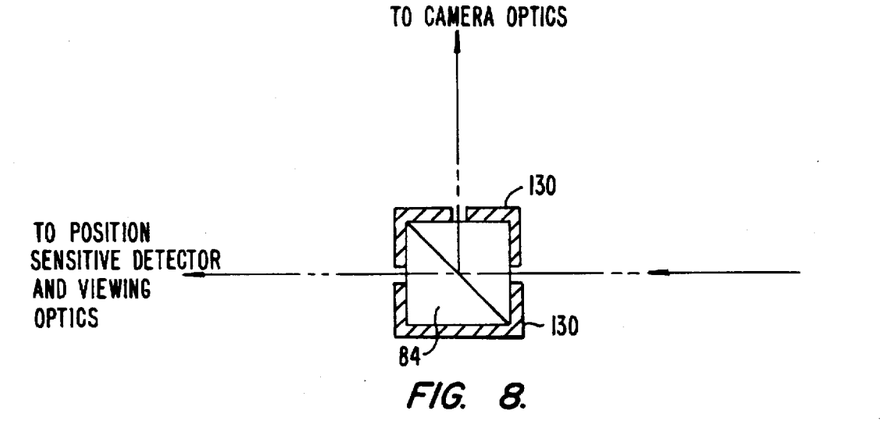
FIG. 8 shows a beamsplitter cube with black glass applied to unused faces.

Beamsplitter cube 84 is positioned slightly off-axis so that unwanted reflections from the faces of beamsplitter cube 84 are skewed out of the optical path of the entering beam. This is accomplished by rotating the beamsplitter cube 1° to 10°, preferably 3° to 5°, about an axis normal to the reflection surface within the cube. Similarly, penta prism 86 is rotated in the plane of reflection to remove unwanted reflections from the field of view. Additionally, to capture stray light from unwanted internal reflections within beamsplitter cube 84, black glass 130 is glued to the unused surfaces of beamsplitter cube 84, as shown in FIG. 8. In this way, only the desired internal reflection of beam 65 and beam 63 exit beamsplitter cube 84.

Figure 5:
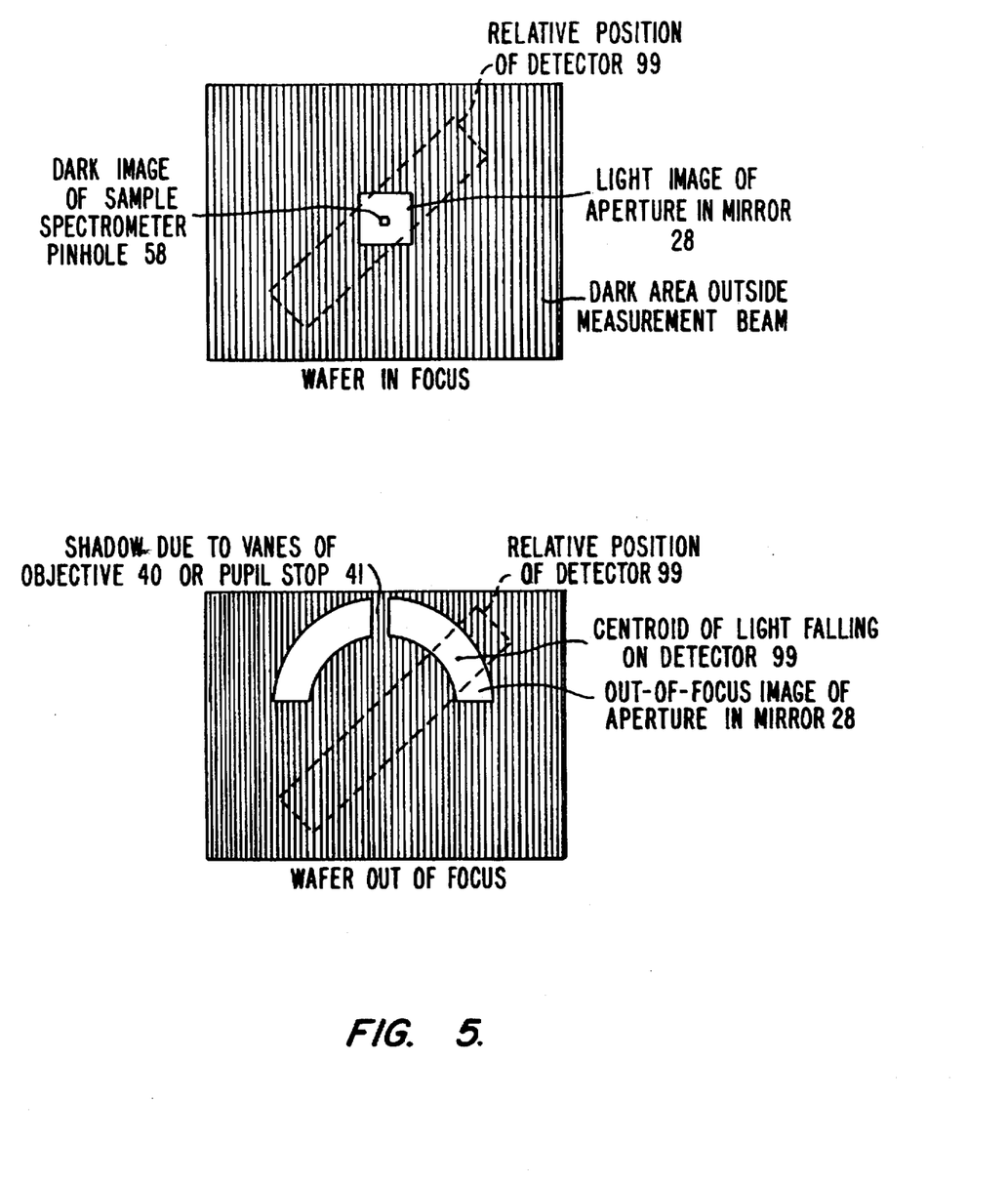
FIG. 5 is an illustration of the light patterns created on a position sensitive focus detector in the autofocus system in a coarse focus mode when a sample is out of focus.

The autofocus subsystem has two modes, a coarse-focus mode to allow for wide range lock-in, and a fine-focus mode for use once a coarse focus is achieved. In the coarse-focus mode, flip-in fine-focus aperture 30 is flipped out of the optical path, and the square aperture of aperture mirror 28 is imaged onto a detector 99, as shown in FIG. 5.

Detector 99 has two outputs, a position output, which is dependent on the position of the centroid of the light falling on detector 99, and an intensity output, which is dependent on the intensity of light falling on detector 99. Detector 99 is also positioned to avoid dark regions of the out-of-focus image, as shown in FIG. 5. In the coarse-focus mode, the centroid of the image falling on detector 99 indicates not only the direction in which focus lies, but also how far out of focus wafer 3 is. The Z position of wafer 3 is then adjusted until the centroid of the light falling on detector 99 is centered near the center of detector 99. With the appropriate positioning and feedback mechanism, wafer 3 can be kept in coarse focus while the wafer is being moved in the X and Y directions. Typically, when the wafer is moving in the X or Y directions, the coarse focus mode is used. Since the wafer can be kept in coarse focus while it is moving from viewing site to viewing site, less time is needed to bring the sample into fine focus at each site. In one embodiment of the present invention, a feedback loop between detector 99 and a servo motor which adjusts the focus is disabled when no light falls on detector 99. This is to prevent uncontrolled movement of the stage supporting wafer 3.

For fine focus, flip-in aperture 30 is flipped into the optical path of measurement beam 25, resulting in a smaller square image reaching detector 99. The smaller square image is 40 82 m with a 1X objective. Since flip-in aperture 30 is the same size as aperture 58, and the two apertures are at conjugates of objective 40, when wafer 3 is in focus, very little light falls outside aperture 58 to be reflected onto detector 99. Thus, in the fine-focus mode, the intensity output of detector 99 is used to bring wafer 3 into focus, with the Z position of wafer 3 being adjusted until the intensity output of detector 99 is minimized.

Figure 6:
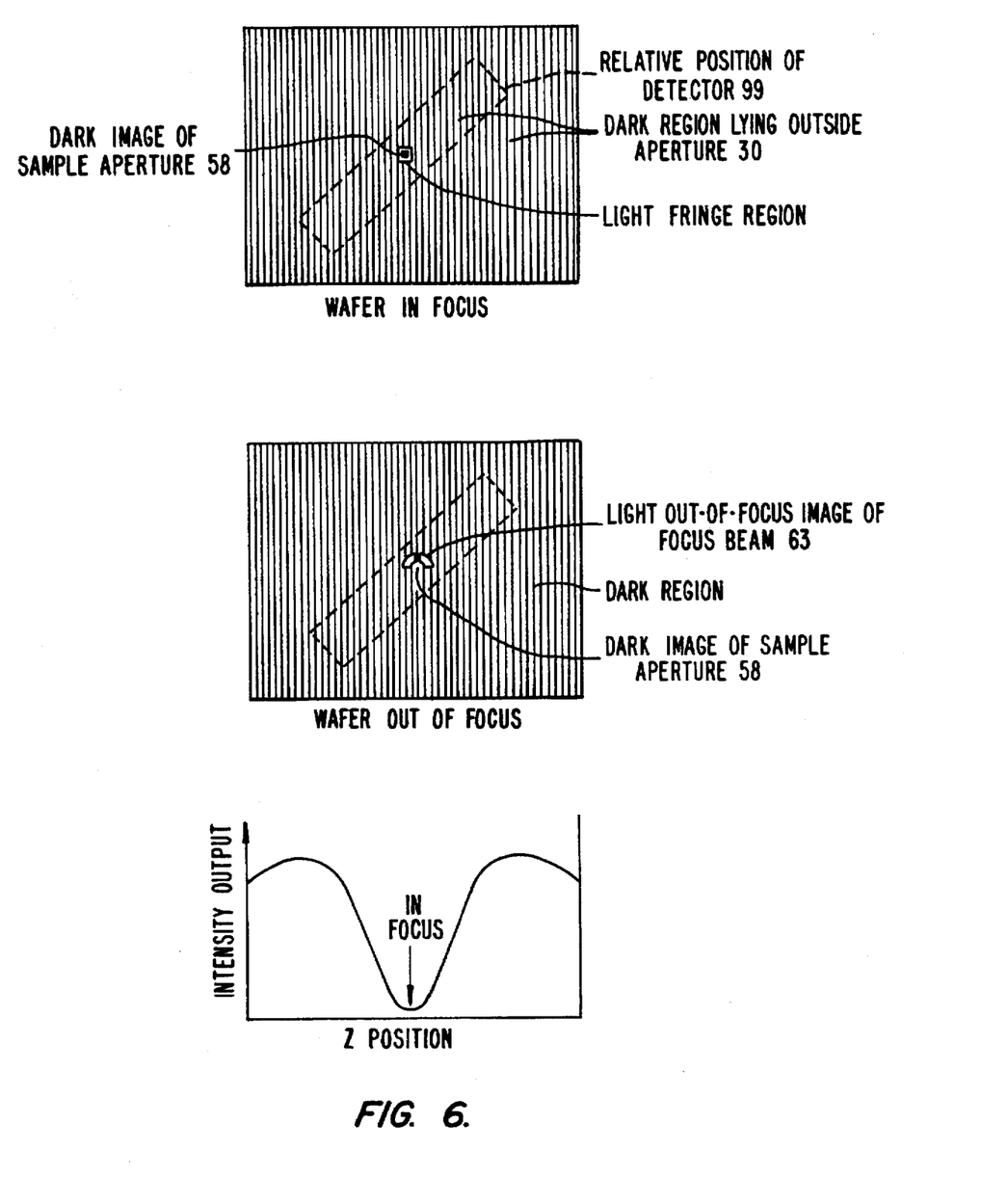
FIG. 6 is an illustration of the light patterns created on a position sensitive focus detector in the autofocus system in a fine-focus mode and the fine focus response as a function of the distance between a sample and an objective.

FIG. 6 illustrates the images falling on detector 99 in the fine-focus mode. When in focus, nearly all the light from aperture 30 (shown in FIG. 6 as the light region) passes through sample aperture 58, leaving only a fringe of light to fall on detector 99. Given ideal optics, all the light from aperture 30 will pass through sample aperture 58, leaving the fringe shown in FIG. 6 infinitesimally thin. An out-of-focus image allows much more light to fall on detector 99 than if wafer 3 were in focus. Consequently, the intensity of light, when plotted versus the Z position of wafer 3 with respect to objective 40, follows the curve shown in FIG. 6.

An embodiment and variations of an optical system according to the present invention has now been described. The above description is illustrative and not restrictive. Many variations of the invention will become apparent to those of skill in the art upon review of this disclosure. Merely by way of example, objective lens 40 could be part of a multiple lens assembly which provides for several magnifications; the Z position for changing X and Y positions could be estimated from a known wafer tilt; the sample being observed need not be a wafer, but could be any other reflective object; fold mirrors can be removed where space allows, and additional fold mirrors can be provided where space is limited. Therefore, the scope of the invention should be determined not with reference to the above descriptions, but instead should be determined with reference to the appended claims along with their full scope of equivalents.

What is claimed is:

1. In an optical system having a platform for supporting a sample, an apparatus for determining the relative reflectance spectrum of a selected area on the sample, comprising:

a light source for emitting a first beam;

a beam splitter for splitting said first beam into a reference beam and a sample beam, said beam splitter being a totally reflecting mirror;

a focussing means for focussing said sample beam at a focal point, the platform movable with respect to said focussing means;

a reference spectroscopic means for detecting a reference spectrum of said reference beam;

a sample spectroscopic means for detecting a reflected spectrum of a reflection of said sample beam, said reflection reflecting off the sample over the selected area; and a computation means for comparing said reflected spectrum and said reference spectrum to determine a relative reflectance spectrum.

2. The apparatus of claim 1, wherein said reference beam illuminates said reference spectroscope means without interacting with said beam splitter.

3. The apparatus of claim 1, wherein said light source emits light over a spectrum of about 220 nm to about 830 nm.

4. The apparatus of claim 1, wherein said reference and sample spectroscopic means each comprise:

an entrance aperture;

a diffraction grating for dispersing light passing through said entrance aperture; and means for detecting a spectrum first order diffraction beam from said diffraction grating, said first order diffraction beam being a diffraction of said light passing through said entrance aperture.

5. The apparatus of claim 4, wherein said diffraction grating of said reference spectroscopic means and said diffraction grating of said sample spectroscopic means comprise a single diffraction grating.

6. The apparatus of claim 4, wherein said diffraction grating is an aberration-corrected holographic diffraction grating.

7. The apparatus of claim 4, wherein said means for detecting a spectrum comprises a linear photodiode array.

8. The apparatus of claim 1, wherein said beam splitter is placed with an edge offset from an optical centerline, said offset placing said beam splitter in less than half of said first beam and said offset being sufficient to reduce vignetting of said reflection by said edge.

9. The apparatus of claim 1, wherein said reference spectroscopic means comprises a first photodiode and said sample spectroscopic means comprises a second photodiode.

10. The apparatus of claim 9, wherein said first photodiode and said second photodiode are sensitive to ultraviolet light.

11. The apparatus of claim 9, further comprising:

a flip-in filtering mirror, flexibly mounted in the optical system to allow placement of said flip-in filtering mirror in at least one spectroscopic light beam and removal therefrom, said flip-in filtering mirror removing visible light from said at least one spectroscopic light beam to form at least one substantially ultraviolet beam, said at least one substantially ultraviolet beam illuminating at least one of said first photodiode and said second photodiode.

12. The apparatus of claim 9, further comprising:

a fixed filtering mirror fixed in a path of at least one spectroscopic light beam, said fixed filtering mirror being substantially transparent to visible light components of said at least one spectroscopic light beam and said fixed filtering mirror reflecting ultraviolet components of said at least one spectroscopic light beam onto at least one of said first photodiode and said second photodiode.

13. The apparatus of claim 9, further comprising:

a flip-in filtering mirror, flexibly mounted in the optical system to allow placement of said flip-in filtering mirror in at least one spectroscopic light beam and removal therefrom, said flip-in filtering mirror removing visible light from said at least one spectroscopic light beam to form at least one substantially ultraviolet beam;

a fixed filtering mirror fixed in a path of said at least one substantially ultraviolet beam, said fixed filtering mirror removing visible light from said at least one substantially ultraviolet beam to form at least one ultraviolet beam, said at least one ultraviolet beam illuminating at least one of said first photodiode and said second photodiode.

14. The apparatus of claim 1, wherein said focussing means comprises an objective lens.

15. The apparatus of claim 1, further comprising a first aperture formed by a first pupil stop and a second aperture formed by a second pupil stop, wherein said first pupil stop and said second pupil stop are coplanar, wherein said sample beam passes through said first aperture before reaching the selected area, and said reflection of said sample beam passes through said second aperture after being reflected from the selected area, and wherein said second aperture is larger than said first aperture.

16. The apparatus of claim 1, wherein said light source also provides field illumination to illuminate a viewing field on the sample.

17. A method for measuring the relative reflectance spectrum of a surface of a sample in an optical system, comprising the steps of:

illuminating an optical path with a light beam;

deflecting less than all of said light beam onto a sample optical path using a mirror placed less than completely across said light beam;

directing light in said optical path onto the surface of the sample;

collecting light reflected from the surface of the sample for spectroscopic measurement;

measuring a reflected spectrum of said light reflected from the surface of the sample;

collecting light which was not deflected in the deflecting step as a reference beam;

measuring a reference spectrum of said reference beam;

comparing said reflected spectrum with said reference spectrum to find a relative reflectance spectrum of the surface of the sample.

18. The method of claim 17, wherein the step of measuring said reflected spectrum comprises measuring a single sample value, and wherein the step of measuring said reference spectrum comprises measuring a single reference value.

19. The method of claim 17, wherein a spectrum comprises values at each of n wavelengths, where n is a positive integer greater than zero, wherein the step of measuring said reflected spectrum comprises measuring a sample value at each of said n wavelengths, wherein the step of measuring said reference spectrum comprises measuring a reference value at each of said n wavelengths, and wherein the step of comparing comprises the steps of dividing, for each wavelength, said sample value by said reference value for each of said n wavelengths, said relative reflectance spectrum comprising n reflectance values.

20. In an optical system, including a movable platform for supporting a sample, an objective lens and a means for moving the movable platform such that a selected area on said sample can be brought into focus with respect to the objective lens, means for autofocusing comprising:

an illumination source which emits a beam of light comprising at least visible light;

a beam shaper for forming a circularly asymmetric beam from said beam of light, said circularly asymmetric beam illuminating and reflecting off the sample near the selected area;

a position sensitive detector for detecting a centroid of at least a portion of said reflected circularly asymmetric beam, said position sensitive detector including an output indicating a separation distance value and a separation direction value between said centroid and a focus point, said focus point being a point on said position sensitive detector where said centroid is located when the sample is in focus with respect to the objective lens; and a signal means, for providing said separation distance value and said separation direction value to the means for moving the movable platform, the means for moving the movable platform responding to said separation distance value and said separation direction value by moving the movable platform to a coarse-focus position 3.

21. The autofocus means of claim 20, wherein said circularly asymmetric beam comprises a beam with a half annular cross section.

22. The autofocus means of claim 20, wherein said illumination source includes an aperture means for limiting light reaching said beam shaper.

23. The autofocus means of claim 20, wherein said illumination source includes a radial uniformer.

24. The autofocus means of claim 20, wherein said illumination source comprises a lamp, an off-axis parabolic mirror for forming a non-diverging beam, and a radial uniformer comprising a silica fiber.

25. The autofocus means of claim 20, wherein said illumination source provides a field illumination beam comprising visible light for illuminating a viewing field on the sample.

26. The autofocus means of claim 20, further comprising means for fine-focusing, wherein said illumination source is limited by a first aperture, wherein said reflected circularly asymmetric beam is reflected off a mirror with an second aperture therein, wherein said first and second apertures are at different conjugate focal points of the objective lens, wherein light reflecting off said mirror is collected by a light intensity detector, and wherein said light intensity detector controls the position of the sample with respect to the objective lens and positions the sample so as to minimize said light collected by said light intensity detector, the sample being substantially in focus when said light collected be said light intensity detector is minimized.

27. The autofocus means of claim 26, wherein said position sensitive detector is also said light intensity detector.

28. The autofocus means of claim 20, further comprising a beam splitter cube, comprising a partially reflecting surface, for deflecting a portion of said circularly asymmetric beam to form a viewing beam, said beam splitter cube mounted at an angle offset from a perpendicular angle to said circularly asymmetric beam.

29. The autofocus means of claim 28, wherein said angle is between about 3 degrees and about 5 degrees.

30. The autofocus means of claim 28, wherein a first coating of black glass is attached to unused surface areas of said beam splitter cube, for absorbing unwanted reflections in said beam splitter cube.

31. The autofocus means of claim 28, further comprising a penta prism in said viewing beam, for deflecting said viewing beam through a right angle with a non-mirrored image, said penta prism mounted at an angle offset from a perpendicular to said viewing beam of between about 3 degrees and about 5 degrees.

32. The autofocus means of claim 31, wherein a first coating of black glass is attached to unused surface areas of said penta prism, for absorbing unwanted reflections in said penta prism.

33. In an optical system having a housing for supporting optical elements and a platform movable relative to the housing for supporting a sample, an apparatus for determining the relative reflectance spectrum of a selected area on the sample, comprising:

a light source for emitting a first beam, said light source comprising a lamp and a radial uniformer comprising a silica fiber, said lamp emitting light with a spectrum of about 220 nm to about 830 nm;

a beam splitter for splitting said first beam into a reference beam and a sample beam, said beam splitter being a totally reflecting mirror;

an objective lens for focussing said sample beam at a focal point, wherein said focal point is within a range of movement of the platform such that the selected area on the sample can be brought into focus with respect to said objective lens;

a reference spectroscopic means for detecting a reference spectrum of said reference beam;

a sample spectroscopic means for detecting a reflected spectrum of a reflection of said sample beam, said reflection reflecting off the sample over the selected area;

a computation means for comparing said reflected spectrum and said reference spectrum to determine a relative reflectance spectrum;

a beam shaper for forming a circularly asymmetric beam from said beam of light, said circularly asymmetric beam illuminating and reflecting off the selected area;

a position sensitive detector for detecting a centroid of at least a portion of said reflected circularly asymmetric beam, said position sensitive detector including an output indicating a separation distance value and a separation direction value between said centroid and a focus point, said focus point being a point on said position sensitive detector where said centroid is located when the sample is in focus with respect to said objective lens;

a signal means, for providing said separation distance value and said separation direction value to the means for moving the platform, the means for moving the platform responding to said separation distance value and said separation direction value by moving the platform to a coarse-focus position;

means for fine-focussing, wherein said light source is limited by a first aperture, wherein said reflected circularly asymmetric beam is reflected off an mirror including a second aperture, wherein said first and second apertures are at different conjugate focal points of the objective lens, wherein light reflecting off said mirror is collected by a light intensity detector, and wherein said light intensity detector controls the position of the sample with respect to the objective lens though movements of the platform and positions the sample so as to minimize said light collected by said light intensity detector, the sample being substantially in focus when said light collected be said light intensity detector is minimized;

a beam splitter cube, comprising a partially reflecting surface, for deflecting a portion of said circularly asymmetric beam to form a viewing beam, said beam splitter cube mounted at an angle of between about 3 degrees and about 5 degrees from perpendicular to said circularly asymmetric beam;

a first coating of black glass attached to unused surface areas of said beam splitter cube, for absorbing unwanted reflections in said beam splitter cube;

a penta prism in said viewing beam, for deflecting said viewing beam through a right angle with a non-mirrored image, said penta prism mounted at an angle of offset from perpendicular to said viewing beam by an angle of between about 3 degrees and about 5 degrees; and a second coating of black glass attached to unused surface areas of said penta prism, for absorbing unwanted reflections in said penta prism.

34. A method for measuring a relative reflectance spectrum of a surface of a sample, comprising:

providing a light beam;

splitting said light beam into a sampling beam and a reference beam;

focusing said sampling beam onto the surface of the sample by means of an objective;

collecting light reflected by the surface of the sample by means of said objective;

measuring a reflected spectrum of the light reflected and collected from the sample;

measuring a reference spectrum of the reference beam; and comparing said reflected spectrum and said reference spectrum to determine a relative reflectance spectrum.

35. The method of claim 34, said splitting including directing the beam to a mirror placed less than completely across said light beam.

36. The method of claim 34, said splitting including deflecting less than all of said light beam to form the sample beam, the undeflected portion of said light beam defining a reference light beam.

37. The method of claim 34, said splitting including forming a circularly asymmetric beam from said beam of light, said asymmetric beam illuminating and reflecting from the sample.

38. The method of claim 37, further comprising detecting a position of the reflected circularly asymmetric beam relative to a reference position.

39. The method of claim 38, further comprising moving the sample in response to said position of the reflected circularly asymmetric beam relative to the reference position.

40. The method of claim 38, said detecting including determining a relative position of a centroid of at least a portion of said reflected circularly asymmetric beam relative to a reference position of said centroid.

41. The method of claim 34, said light beam and said reflected and reference spectra including multiple wavelengths.

42. The method of claim 41, said multiple wavelengths within a range from about 220 nm to about 830 nm.

43. An apparatus for measuring a relative reflectance spectrum of a surface of a sample, comprising:

a light source providing a light beam;

a beam splitter splitting said light beam into a sampling beam and a reference beam;

an objective focusing said sampling beam onto the surface of the sample and collecting light reflected from the surface of the sample;

a sample spectroscopic device measuring a reflected spectrum of the light reflected from the sample and collected by the objective;

a reference spectroscopic device measuring a reference spectrum of the reference beam; and means for comparing said reflected spectrum and said reference spectrum to determine a relative reflectance spectrum.

44. The apparatus of claim 43, said beam splitter including a totally reflecting mirror placed less than completely across said light beam.

45. The apparatus of claim 43, said beam splitter deflecting less than all of said light beam to form the sample beam, the undeflected portion of said light beam defining a reference light beam.

46. The apparatus of claim 43, said beam splitter forming a circularly asymmetric beam from said beam of light, said circularly asymmetric beam illuminating and reflecting from the sample.

47. The apparatus of claim 46, further comprising a position sensitive detector detecting a position of the reflected circularly asymmetric beam relative to a reference position.

48. The apparatus of claim 47, further comprising means for moving the sample in response to said position of the reflected circularly asymmetric beam relative to the reference position.

49. The apparatus of claim 47, said detector detecting a relative position of a centroid of at least a portion of said reflected circularly asymmetric beam relative to a reference position at the detector.

50. The apparatus of claim 43, said light beam and said reflected and reference spectra including multiple wavelengths.

51. The apparatus of claim 50, said multiple wavelengths within a range from about 220 nm to about 830 nm.

52. A method for autofocusing a light beam onto a sample, comprising:

directing a circularly asymmetric light beam to illuminate the sample, said beam reflecting from the sample to form a reflected beam;

detecting a relative position of a centroid of at least a portion of said reflected beam relative to a reference position; and moving the sample in response to said relative position of the centroid to the reference position.

53. The method of claim 52, wherein said directing directs a light beam containing visible light to the sample.

54. A apparatus for autofocusing a light beam onto a sample, comprising:

a source supplying a circularly asymmetric light beam to illuminate the sample, said beam reflecting from the sample to form a reflected beam;

a detector detecting a relative position of a centroid of at least a portion of said reflected beam relative to a reference position; and means for moving the sample in response to said relative position of the centroid to the reference position.

55. The apparatus of claim 54, wherein said source supplies visible light to the sample.

56. The apparatus of claim 54, said detector being a position sensitive detector.

57. The apparatus of claim 54, wherein said source supplies a beam with a half annular cross-section.

\* \* \* \* \*